US00PP08626P

United States Patent [19]

de Ruiter

[11] Patent Number: Plant 8,626

[45] Date of Patent: Mar. 8, 1994

[54] MINIATURE ROSE PLANT NAMED RUINERO

[75] Inventor: Gijsbert de Ruiter, Hazerswoude, Netherlands

[73] Assignee: de Ruiter's Nieuwe Rozen B.V., Hazerswoude, Netherlands

[21] Appl. No.: 999,604

[22] Filed: Dec. 31, 1992

[51] Int. Cl.[5] ..... A01H 5/00

[52] U.S. Cl. ..... Plt./7.1

[58] Field of Search ..... Plt. 7.1, 9, 10, 10.1

*Primary Examiner*—Howard J. Locker

*Attorney, Agent, or Firm*—Christie, Parker & Hale

[57] ABSTRACT

A new variety of miniature rose plant having small orange red flowers produced on a good pot-forcing plant.

SUMMARY OF THE INVENTION

The present invention relates to a new and distinct variety of rose plant of the miniature rose class, which was originated by me by crossing as the seed and pollen parents unnamed and unpatented seedlings of my creation. The varietal denomination of the new variety is 'Ruinero'.

Amont the novel characteristics possessed by this new variety which distinguish it from its parent and all other varieties of which I am aware are its attractive, small orange red flowers borne on a floriferous plant particularly suited for production of flowering pot plants. The new variety can be reproduced through propagation by cuttings, grafting, budding, and micropropagation. Flowers of the new variety are long-lasting on the plant. Asexual reproduction by budding, grafting and propagation of cuttings of the new variety as performed in Hazerswoude, Holland shows that the foregoing and other distinguishing characteristics come true to form and are established and transmitted through succeeding propagations.

2 Drawing Sheets

BRIEF DESCRIPTION OF ILLUSTRATIONS

The accompanying illustrations show typical specimens of the vegetative growth and flowers of the new variety in different stages of development depicted in color as nearly true as it is reasonably possible to make the same in a color illustration of this character. Phenotypic expression, including colors, may vary depending upon growth conditions, such as under different climate, soil, and cultivation conditions.

One accompanying illustration is of a plant of the new variety of miniature rose showing flowering and growth habit. The other illustration shows details of the new miniature rose variety.

DETAILED DESCRIPTION OF THE NEW VARIETY

The following is a detailed description of my new variety, with color terminology in accordance with The Royal Horticultural Society Colour Chart (R.H.S.C.C.) and horticultural terminology in accordance with standard terminology used in UPOV-approved horticultural guidelines. The terminology used in color descriptions herein refers to plate numbers in the aforementioned color chart.

Parentage: Seedling.

*Seed parent.*—Unnamed seedling.

*Pollen parent.*—Unnamed seedling.

Class: Miniature.

As can be seen in the accompanying illustrations, one illustration shows a specimen of flowering plant of the new variety depicting the pot plant flowering and growth habits. Since flowering is nearly continuous, this floriferous variety can remain attractively in bloom for long periods when given proper care and culture.

The other illustration shows details of the new variety. In the illustration there is shown the top of a young shoot, 1; compound three and five leaflet leaves, 2 and 3, respectively; a stem, 5; buds, 6 and 7; a flower, 8, about one-half open; and a flower 9, fully open. Also shown are portions of flower stems 10, 11 and 12, with reproductive organs displayed.

The following further horitcultural observations were made of specimens grown under glass in Holland.

FLOWER

Blooming habit: Nearly continuous.

A. Bud:

(1) *Size.*—Medium.

(2) *Form.*—Ovate (before separation of sepals); broad obovate after sepals part.

(3) *Color.*—As sepals divide, bud color is near 43A to 43B.

(4) *Sepals.*—Longer than bud, simple to slightly foliated.

(5) *Peduncle.*—Length — medium for miniature. Aspect — straight. Strength — erect. Color — medium green.

B. Bloom:

*Flower.*—Medium size for miniature; viewed from above — round; viewed from side, (a) upper part of fully opened flower, flattened convex; (b) lower part of fully opened flower, concave.

(1) *Size.*—Average size when fully expanded — about 5 cm.

(2) *Borne.*—Primarily singly, one to a stem.

(3) *Form.*—Ovoid, becoming flat; outer petals quill to points, inner petals roll under slightly.

(4) *Petalage.*—Many-petaled under normal conditions — semi-double.

(5) *Color.*—After sepals separate and part and petals being to unfurl, color of outer petals is near 48C to D; top surface of inner petals tends to be near 43B to D at center where petals bunch; reverse surface tends to be similar to top surface. Coloring at point of petal attachment is near 4B. Overall tonality from a distance is attractive orange red. Flower color tends to lighten upon aging.

(6) *Pedicel.*—Very few hairs or prickles.

(7) *Fragrance.*—Slight to none.

Petals:

(1) *Texture.*—Very good substance.

(2) *Appearance.*—Inside velvety and outside satiny.

(3) *Form and size.*—Medium for miniature, obovate.

(4) *Arrangement.*—Regularly arranged, imbricated.

(5) *Petaloids in center.*—Few.

(6) *Lasting quality.*—Long lasting quality on plant.

(7) *Petalage.*—About 20.

Reproductive Organs

A. Stamens, filaments and anthers:

*Arrangement and color.*—Regularly arranged around styles; color filaments — yellow to yellow green.

B. Pollen:

*Color.*—Pale yellow.

C. Styles: Short, white to pale green, generally not hairy.

D. Stigmas: Positioned at same level to below anthers.

E. Hips: Very small, pitcher-shaped.

Plant

A. Form: Upright, bushy.

B. Growth: Vigorous, about 30 cm in height.

C. Foliage: Compound 3 and 5 leaflets.

(1) *Size.*—Medium for a miniature.

(2) *Quantity.*—Abundant.

(3) *Color.*—Foliage at time of first flowering — light to medium green, near 138A to B.

(4) *Shape.*—Oval, pointed.

(5) *Texture.*—Upper side is weak glossy; underside is matte.

(6) *Edge.*—Serrate.

(7) *Serration.*—Ordinary, acuminate apices.

(8) *Leaf stem.*—Color — medium green.

(9) *Stipules.*—Ordinary, medium to long, medium green, distinct auricle.

(10) *Leaflets.*—Cross section — slight concave, little or no undulation at margin; terminal leaflet (blade) — very short, very narrow, obtuse base; petiole — medium.

D. Wood:

(1) *New wood.*—Color — light to medium green, little or no anthocyanin coloration.

(2) *Old wood.*—Color — medium green.

E. Prickles (thorns):

(1) *Prickles.*—Present, quantity (main stalk) — ordinary; On laterals from stalk — few to none; Form — straight; Shape of upper side — flat; Shape of lower side — deep, concave; Color — tan; Position — irregular.

I claim:

1. A new and distinct variety of rose plant of the miniature rose class, substantially as shown and described.

* * * * *

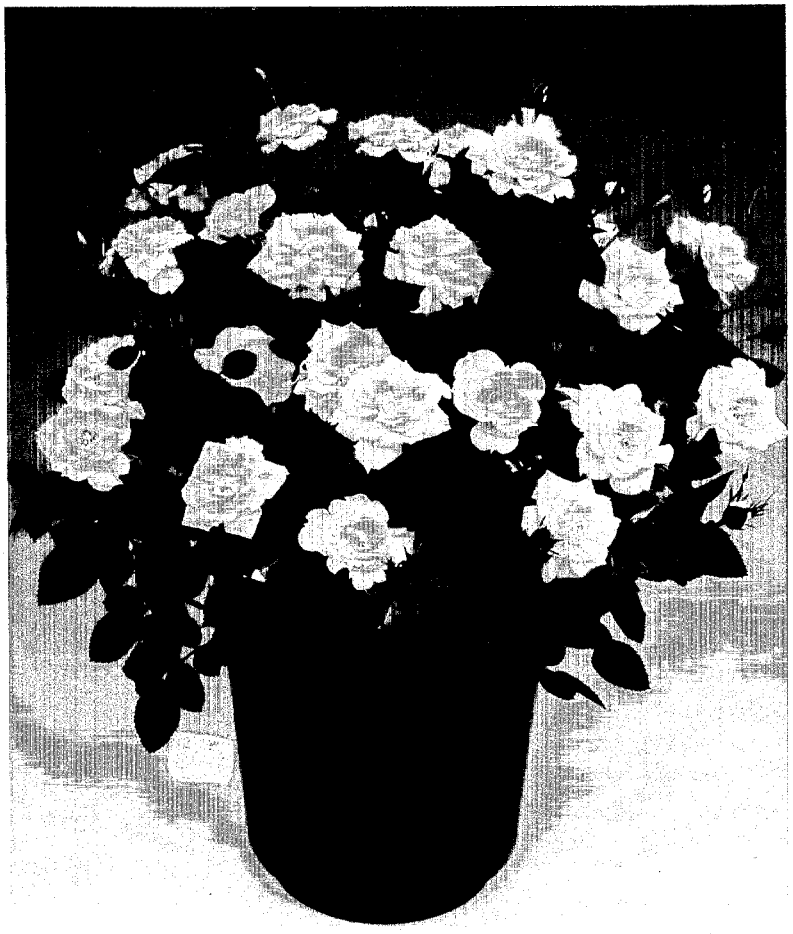

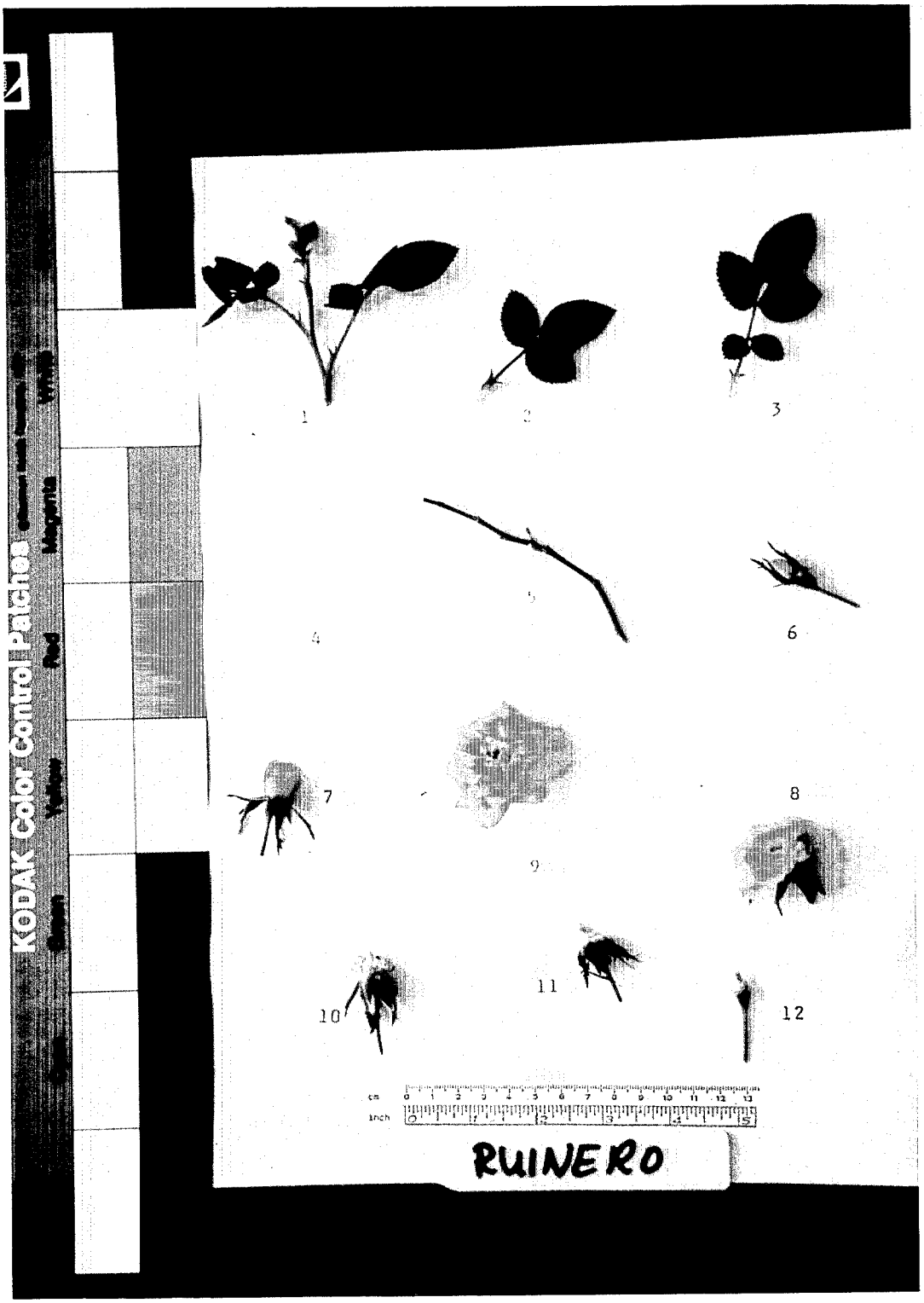
KODAK Color Control Patches
1
2
3
4
5
6
7
8
9
10
11
12
cm
inch
RUINERO